United States Patent [19]

Donatiello

[11] Patent Number: 5,994,403
[45] Date of Patent: Nov. 30, 1999

[54] TANNIN (TANNIC ACID) TREATMENT OF ATHLETE'S FOOT AND OTHER FUNGAL INFECTIONS

[76] Inventor: Steven T. Donatiello, 707 N. Forest Ave., St. Louis, Mo. 63119-1927

[21] Appl. No.: 08/992,783

[22] Filed: Dec. 17, 1997

[51] Int. Cl.⁶ .............................. A61K 31/19; A61K 33/32
[52] U.S. Cl. ........................ 514/557; 514/858; 424/641; 424/642
[58] Field of Search ................................ 514/557, 574, 514/858; 424/195.1, 641, 642

[56] References Cited

U.S. PATENT DOCUMENTS 5,420,114  5/1995  Clodman et al. ..................... 514/23

FOREIGN PATENT DOCUMENTS 9715282  5/1997  WIPO .

*Primary Examiner*—Kevin E. Weddington

[57] ABSTRACT

Tannic acid solution either alone or in conjunction with zinc oxide provides a treatment for fungal infections of the skin and nails.

4 Claims, No Drawings

TANNIN (TANNIC ACID) TREATMENT OF ATHLETE'S FOOT AND OTHER FUNGAL INFECTIONS

CROSS REFERENCE TO RELATED APPLICATIONS

Reference is made to U.S. Pat. No. 2,100,054 as it discusses some of the properties of tannic acid as it relates to being an astringent, antiseptic, disinfectant, and treatment of burns. It also discusses the fact that tannic acid is readily biodegradable and of low toxicity and hence ideal for direct application to skin.

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

The idea for this invention came from several sources.

1. I noted that tannin(tannic acid) was highly resistive to biodegradation based on some groundwater monitoring work that I had conducted. I inferred from this that this material must be a natural toxin for single cell organisms.

However, since tannin is non-toxic, I thought that there had to be some use for this material which is extracted from plant material.

2. I noted that healthy trees are actually able to halt and reverse the spread of fungal infections. I presumed that was due to a material produced by a healthy tree. Research indicated that trees produce tannins.

Tannin(tannic acid), which is extracted from tree bark, is used to tan leather. This process of tanning leather actually impregnates the leather with tannin which are families of hydrolyzable galloyl tannins. These materials remove free water from the outer layer of skin and toughen the skin with tannins which are highly resistive to attack by the fungi which cause athletes foot and other similar infections.

3. Zinc Oxide is also widely used to fight infections and in proper balance with tannic acid produces a product which with several treatments, eliminates athlete's foot and prevents its reoccurrence. Its effect, similar to tannins is to place a difficult to degrade material, on the skin surface. This makes the skin surface less susceptible to fungal attack.

4. Testing has shown that 3 successive foot soakings in 100–120 degrees Fahrenheit water with a high concentration of tannin acid and lower concentration of zinc oxide will prevent the spread of and eventually eliminate athlete's foot and other fungal infections.

5. Similarly, a solution of 25% tannin, either alone or in combination with lesser dosages of zinc oxide is effective in the treatment of a variety of fungal infections, primarily athlete's foot.

BRIEF SUMMARY OF THE INVENTION

1. The use of tannin acid solution for the treatment of fungal skin infections, either alone or in combination with zinc oxide.

2. This is an all natural treatment, non-toxic, which contrasts with existing pharmacological treatments which depend upon highly toxic organic chemicals.

3. This treatment is far more effective in that it converts the skin surface into a surface which is highly resistive to fungal attack. This process partially tans the skin surface.

BRIEF DESCRIPTION OF THE SEVERAL VIEWS OF THE DRAWING

Not Applicable.

DETAILED DESCRIPTION OF THE INVENTION

The invention is a new use for existing materials, Tannic Acid and Zinc Oxide. Specifically, a 10–25% solution of Tannic Acid (with 1–5% Zinc Oxide optional), creates a solution which when applied to skin, tans the skin so that fungal infections are prevented.

In cases where a fungal infection is active, this treatment acts as an antiseptic, astringent, and tanning agent such that spread of the infection is limited and eventually the infection is unable to spread and dies out.

What is claimed is:

1. An antifungal composition for the treatment of fungal skin infections consists of a tannic acid solution comprising tannic acid and water.

2. An antifungal composition for the treatment of Athlete's Foot, and other fungal infections on skin, toenails, and fingernails contains a tannic acid solution comprising tannic acid, zinc oxide, and water.

3. A method for treating athlete's foot or fungal infections on the skin, toenails, and fingernails consists of a tannic solution comprising tannic acid and water.

4. A method for treating athlete's foot or fungal infection on the skin, toenails, and fingernails consists of a tannic acid solution comprising tannic acid, zinc oxide and water.

* * * * *